US007812122B2

(12) United States Patent
Assadi-Porter

(10) Patent No.: US 7,812,122 B2
(45) Date of Patent: Oct. 12, 2010

(54) PROTEIN SWEETENER

(75) Inventor: Fariba M. Assadi-Porter, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 411 days.

(21) Appl. No.: 12/033,120

(22) Filed: Feb. 19, 2008

(65) Prior Publication Data

US 2008/0281077 A1    Nov. 13, 2008

Related U.S. Application Data

(60) Provisional application No. 60/918,203, filed on Mar. 15, 2007.

(51) Int. Cl.
*C07K 14/00* (2006.01)
(52) U.S. Cl. .................................................. 530/324
(58) Field of Classification Search ........................ None
See application file for complete search history.

(56) References Cited

U.S. PATENT DOCUMENTS

| 5,326,580 | A  | 7/1994  | Hellekant et al. |
| 5,346,998 | A  | 9/1994  | Hellekant et al. |
| 5,527,555 | A  | 6/1996  | Hellekant et al. |
| 5,741,537 | A  | 4/1998  | Hellekant et al. |
| 6,274,707 | B1 | 8/2001  | Markley et al. |
| 7,153,535 | B2 | 12/2006 | Jin et al. |

FOREIGN PATENT DOCUMENTS

| WO | WO 94/19467 | 9/1994 |
| WO | WO 95/31547 | 11/1995 |
| WO | WO 00/61759 | 10/2000 |

OTHER PUBLICATIONS 5 pages of ISR and associated Invitation dated Jan. 9, 2009 in connection with the corresponding PCT/U.S. 2008/055913.
Markley, J., et al.; "Solution Structure of the Thermostable Sweet-Tasting Protein Brazzein", Nature Structure Biology, vol. 5, No. 6, Jun. 1998, pp. 427-431.
Assadi-Porter, F., et al.; "Efficient Production of Recombinant Brazzein . . . ", Archives of Biochemistry and Biophysics, vol. 376, No. 2, Apr. 15, 2000, pp. 252-258.
Hellekant, et al.; "Characterization and Chemical Modication of Brazzien . . . ", Acta Botanica Yunnanica, 1996; 18 (2): 123-133.
Jin, Z., et al.; "Monkey Electrophysiological and Human Psychophysical Responses to Mutants of the Sweet Protein Brazzein . . . ", Chem. Senses 28: 491-498, 2003.
Jin, Z., et al.; "Critical Regions for the Sweetness of Brazzein", FEBS Letters 544 (2003 33-37.
Assadi-Porter, F., et al.; "Sweetness Determinant Sites of Brazzein . . . ", Archives of Biochemistry and Biophysics, vol. 376, No. 2, Apr. 15, 2000, pp. 259-265.
Butt, T. R., et al.; "SUMO fusion technology for difficult-to-express proteins", Protein Expression and Purification 43 (2005) 1-9.
Izawa, H., et al.; "The Structure-Activity Relationships of the Sweet Protein Brazzein . . . ", Peptide Science—Present and Future, 1999, pp. 750-751.
Assadi-Porter et al. J. Mol. Biol., 2010—article in press, "Key Amino Acid Residues Involved in Multi-Point Binding Interactions between Brazzein, a Sweet Protein, and the T1R2-T1R3 Human Sweet Receptor".
8 pages of an international preliminary report dated Sep. 15, 2009 in connection with the corresponding PCT/U.S. 2008/055913.

*Primary Examiner*—Christina Bradley
(74) *Attorney, Agent, or Firm*—Quarles & Brady, LLP

(57) ABSTRACT

Disclosed herein are sweet proteins that are variants of Brazzein, and nucleotide sequences capable of expressing them. Through a replacement of a tyrosine residue at the C terminus in the naturally occurring Brazzein sequence, or the insertion of two residues (at least one being isoleucine, glycine or proline) before the N terminus of wild type Brazzein, sweetness potency, the taste profile and sweetness strength are improved.

8 Claims, 1 Drawing Sheet

SEQUENCE LISTING

```
<160> NUMBER OF SEQ ID NOS: 20

<210> SEQ ID NO 1
<211> LENGTH: 53
<212> TYPE: PRT
<213> ORGANISM: Pentadiplandra brazzeana

<400> SEQUENCE: 1

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 2
<211> LENGTH: 53
<212> TYPE: PRT
<213> ORGANISM: ARTIFICIAL
<220> FEATURE:
<223> OTHER INFORMATION: SYNTHETIC PEPTIDE
<220> FEATURE:
<221> NAME/KEY: misc_feature
<222> LOCATION: (53)..(53)
<223> OTHER INFORMATION: Xaa can be any naturally occurring amino acid

<400> SEQUENCE: 2

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Lys Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Xaa
    50

<210> SEQ ID NO 3
<211> LENGTH: 55
<212> TYPE: PRT
<213> ORGANISM: ARTIFICIAL
<220> FEATURE:
<223> OTHER INFORMATION: SYNTHETIC PEPTIDE
<220> FEATURE:
<221> NAME/KEY: misc_feature
<222> LOCATION: (1)..(2)
<223> OTHER INFORMATION: Xaa can be any naturally occurring amino acid
```

-continued

<400> SEQUENCE: 3

Xaa Xaa Asp Lys Cys Lys Lys Val Tyr Glu Asn Tyr Pro Val Ser Lys
1               5                   10                  15

Cys Gln Leu Ala Asn Gln Cys Asn Tyr Asp Cys Lys Leu Asn Lys His
            20                  25                  30

Ala Arg Ser Gly Glu Cys Phe Tyr Asp Glu Lys Arg Asn Leu Gln Cys
        35                  40                  45

Ile Cys Asp Tyr Cys Glu Tyr
    50                  55

<210> SEQ ID NO 4
<211> LENGTH: 53
<212> TYPE: PRT
<213> ORGANISM: ARTIFICIAL
<220> FEATURE:
<223> OTHER INFORMATION: SYNTHETIC PEPTIDE

<400> SEQUENCE: 4

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Lys Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Phe
    50

<210> SEQ ID NO 5
<211> LENGTH: 53
<212> TYPE: PRT
<213> ORGANISM: ARTIFICIAL
<220> FEATURE:
<223> OTHER INFORMATION: SYNTHETIC PEPTIDE

<400> SEQUENCE: 5

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Lys Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Trp
    50

<210> SEQ ID NO 6
<211> LENGTH: 53
<212> TYPE: PRT
<213> ORGANISM: ARTIFICIAL
<220> FEATURE:
<223> OTHER INFORMATION: SYNTHETIC PEPTIDE

<400> SEQUENCE: 6

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Lys Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu His
    50

<210> SEQ ID NO 7
<211> LENGTH: 55
<212> TYPE: PRT
<213> ORGANISM: ARTIFICIAL
<220> FEATURE:
<223> OTHER INFORMATION: SYNTHETIC PEPTIDE

<400> SEQUENCE: 7

Ile Ile Asp Lys Cys Lys Lys Val Tyr Glu Asn Tyr Pro Val Ser Lys
 1               5                  10                  15

Cys Gln Leu Ala Asn Gln Cys Asn Tyr Asp Cys Lys Leu Asn Lys His
            20                  25                  30

Ala Arg Ser Gly Glu Cys Phe Tyr Asp Glu Lys Arg Asn Leu Gln Cys
        35                  40                  45

Ile Cys Asp Tyr Cys Glu Tyr
    50                  55

<210> SEQ ID NO 8
<211> LENGTH: 55
<212> TYPE: PRT
<213> ORGANISM: ARTIFICIAL
<220> FEATURE:
<223> OTHER INFORMATION: SYNTHETIC PEPTIDE

<400> SEQUENCE: 8

Gly Pro Asp Lys Cys Lys Lys Val Tyr Glu Asn Tyr Pro Val Ser Lys
 1               5                  10                  15

Cys Gln Leu Ala Asn Gln Cys Asn Tyr Pro Cys Lys Leu Asn Lys His
            20                  25                  30

Ala Arg Ser Gly Glu Cys Phe Tyr Asp Glu Lys Arg Asn Leu Gln Cys
        35                  40                  45

Ile Cys Asp Tyr Cys Glu Tyr
    50                  55

<210> SEQ ID NO 9
<211> LENGTH: 159
<212> TYPE: DNA
<213> ORGANISM: ARTIFICIAL
<220> FEATURE:
<223> OTHER INFORMATION: SYNTHETIC NUCLEOTIDE

<400> SEQUENCE: 9
gacaaatgta aaaagtata cgaaaactac ccgtatcca aatgtcagct ggcaaaccag      60
tgtaactacg actgtaaact ggacaaacac gctcgttccg gtgaatgctt ctacgacgaa    120
aaacgtaacc tgcagtgcat ctgcgactac tgcgaattc                           159

<210> SEQ ID NO 10
<211> LENGTH: 159
<212> TYPE: DNA
<213> ORGANISM: ARTIFICIAL
<220> FEATURE:
<223> OTHER INFORMATION: SYNTHETIC NUCLEOTIDE

<400> SEQUENCE: 10
gacaaatgta aaaagtata cgaaaactac ccgtatcca aatgtcagct ggcaaaccag      60
tgtaactacg actgtaaact ggacaaacac gctcgttccg gtgaatgctt ctacgacgaa    120
aaacgtaacc tgcagtgcat ctgcgactac tgcgaatgg                           159

<210> SEQ ID NO 11
<211> LENGTH: 159
<212> TYPE: DNA
<213> ORGANISM: ARTIFICIAL
<220> FEATURE:
<223> OTHER INFORMATION: SYNTHETIC NUCLEOTIDE

<400> SEQUENCE: 11
gacaaatgta aaaagtcta cgaaaactac ccggtatcca aatgtcagct ggcaaaccag    60
tgtaactacg actgtaaact ggacaaacac gctcgttccg gtgaatgctt ctacgacgaa   120
aaacgtaacc tgcagtgcat ctgcgactac tgcgaacac                          159

<210> SEQ ID NO 12
<211> LENGTH: 165
<212> TYPE: DNA
<213> ORGANISM: ARTIFICIAL
<220> FEATURE:
<223> OTHER INFORMATION: SYNTHETIC NUCLEOTIDE

<400> SEQUENCE: 12
atcatcgaca aatgtaaaaa agtatacgaa aactacccgg tatccaaatg tcagctggca    60
aaccagtgta actacgactg taaactggac aaacacgctc gttccggtga atgcttctac   120
gacgaaaaac gtaacctgca gtgcatctgc gactactgcg aatac                   165

<210> SEQ ID NO 13
<211> LENGTH: 165
<212> TYPE: DNA
<213> ORGANISM: ARTIFICIAL
<220> FEATURE:
<223> OTHER INFORMATION: SYNTHETIC NUCLEOTIDE

<400> SEQUENCE: 13
ggtccggaca aatgtaaaaa agtatacgaa aactacccgg tatccaaatg tcagctggca    60
aaccagtgta actacgactg taaactggac aaacacgctc gttccggtga atgcttctac   120
gacgaaaaac gtaacctgca gtgcatctgc gactactgcg aatac                   165

<210> SEQ ID NO 14
<211> LENGTH: 27
<212> TYPE: DNA
<213> ORGANISM: ARTIFICIAL
<220> FEATURE:
<223> OTHER INFORMATION: SYNTHETIC NUCLEOTIDE PCR PRIMER

<400> SEQUENCE: 14
gactactgcg aattctaggg atccggc                                       27

<210> SEQ ID NO 15
<211> LENGTH: 27
<212> TYPE: DNA
<213> ORGANISM: ARTIFICIAL
<220> FEATURE:
<223> OTHER INFORMATION: SYNTHETIC NUCLEOTIDE PCR PRIMER

<400> SEQUENCE: 15
gactactgcg aatggtaggg atccggc                                       27

<210> SEQ ID NO 16
<211> LENGTH: 27
<212> TYPE: DNA
<213> ORGANISM: ARTIFICIAL
<220> FEATURE:
<223> OTHER INFORMATION: SYNTHETIC NUCLEOTIDE PCR PRIMER

-continued

```
<400> SEQUENCE: 16
gactactgcg aacactaggg atccggc                                    27

<210> SEQ ID NO 17
<211> LENGTH: 45
<212> TYPE: DNA
<213> ORGANISM: ARTIFICIAL
<220> FEATURE:
<223> OTHER INFORMATION: SYNTHETIC NUCLEOTIDE PCR PRIMER

<400> SEQUENCE: 17
gctgattcag gtcaacatat gatcgacaaa tgtaaaaaag tatac                45

<210> SEQ ID NO 18
<211> LENGTH: 48
<212> TYPE: DNA
<213> ORGANISM: ARTIFICIAL
<220> FEATURE:
<223> OTHER INFORMATION: SYNTHETIC NUCLEOTIDE  PCR PRIMER

<400> SEQUENCE: 18
gctgattcag gtcaacatat gatcatcgac aaatgtaaaa aagtatac             48

<210> SEQ ID NO 19
<211> LENGTH: 45
<212> TYPE: DNA
<213> ORGANISM: ARTIFICIAL
<220> FEATURE:
<223> OTHER INFORMATION: SYNTHETIC NUCLEOTIDE PCR PRIMER

<400> SEQUENCE: 19
gctgattcag gtcaacatat gggtgacaaa tgtaaaaaag tatac                45

<210> SEQ ID NO 20
<211> LENGTH: 48
<212> TYPE: DNA
<213> ORGANISM: ARTIFICIAL
<220> FEATURE:
<223> OTHER INFORMATION: SYNTHETIC NUCLEOTIDE PCR PRIMER

<400> SEQUENCE: 20
gctgattcag gtcaacatat gggtccggac aaatgtaaaa aagtatac             48
```

US 7,812,122 B2

PROTEIN SWEETENER

CROSS-REFERENCE TO RELATED APPLICATIONS

This application claims the benefit of U.S. provisional patent application 60/918,203 filed Mar. 15, 2007.

STATEMENT REGARDING FEDERALLY SPONSORED RESEARCH/DEVELOPMENT

This invention was made with United States government support awarded by the following agency: NIH Grant no. DC006016. The United States government has certain rights in this invention.

BACKGROUND OF THE INVENTION

The present invention relates to sweet proteins. Specifically, this invention relates to Brazzein protein that has been modified to provide a candy-like taste with high potency.

The most widely used natural sweetener, sugar (sucrose), has significant problems associated with its use (especially causing weight gain by users). Many other sweeteners either have undesirable side effects or are deficient in certain respects. For example, aspartame loses its sweetness when exposed to elevated temperatures for long periods. This renders aspartame unsuitable for use in most baking applications.

Moreover, most existing artificial sweeteners have temporal sweetness profiles which do not adequately match that of sugar. For example, their sweetness may die out sooner or leave an undesirable after taste, and/or may be perceived sooner than sugar. It may therefore be desirable to mix an existing artificial sweetener with one or more other sweeteners having different temporal profiles (so as to create a mixed sweetener that more closely matches the overall temporal sweetness profile of sugar).

Only relatively few sweet proteins (as distinguished from sweet carbohydrates) have been found in nature. One protein that appears to be particularly promising is Brazzein (SEQ ID NO: 1). See also U.S. Pat. Nos. 5,326,580, 5,346,998, 5,527,555 and 5,741,537, PCT publications WO 94/19467 and 95/31547, and J. Caldwell et al., Solution Structure Of The Thermostable Sweet-tasting Protein Brazzein, 5 Nature Structural Biology 427-431 (1998), F. Assadi-Porter et al., Efficient Production Of Recombinant Brazzein, A Small, Heat-Stable, Sweet-Tasting Protein Of Plant Origin, 376 Arch. Biochem Biophys. 252-258 (2000), and G. Hellekant, Characterization And Chemical Modification Of Brazzein, A High Potency Thermostable Sweet Protein From Pentadiplandra Brazzeana, 18 Acta Botanica Yunnanica 123-133 (1996); F. Assadi-Porter et al., Correlation Of The Sweetness Of The Protein Brazzein With Patterns Of Hydrogen Bonds Detected By NMR Spectroscopy, 278 J. Biol. Chem. 31331-9 (2003); F. Assadi-Porter et al., Brazzein, A Small, Sweet Protein: Effects Of Mutations On Its Structure, Dynamics And Functional Properties, 30 Suppl. 1 Chem. Senses i90-i91 (2005). The disclosure of these publications and of all other publications referred to herein are incorporated by reference as if fully set forth herein.

This protein is a 53 amino acid residue protein, but also sometimes appears in nature linked at its N terminal to Glu. In any event, it is particularly desirable because it is stable when subjected to the level of heat typically present during baking of foods. However, there are some concerns regarding its temporal profile, the amount of the sweetener needed for threshold perception, and the perceived nature of the sweetness.

As described in WO 00/61759, and U.S. Pat. No. 6,274,707, attempts were made to improve certain sweetness characteristics of Brazzein through the substitution of Ala or Arg in replacement for an existing amino acid, and/or the addition of Ala or Arg, and/or the truncation of an existing terminal amino acid, of Brazzein. Some of these changes increased sweetness potency, while others decreased it.

Similarly, in H. Izawa et al. Pept. Sci.: Present Future, Proc. Int. Pept. Symp., 1st (1999)(Ed. Y. Shimonishi) there was a description of Ala substitutions for certain amino acids of Brazzein, with some results showing increased sweetness, while others showed decreased sweetness.

In U.S. Pat. No. 7,153,535 there was a discussion of the replacement of particular residues with Lys or Asn as positively affecting sweetness.

In Z. Jin et al., Monkey Electrophysiological and Human Psychophysical Responses to Mutants of the Sweet Protein Brazzein: Delineating Brazzein Sweetness, 28 Chem. Senses 491-498 (2003); Z. Jin et al., Critical Regions For The Sweetness Of Brazzein, 544 FEBS Letters 33-37 (2003); and F. Assadi-Porter et al., Sweetness Determinant Sites Of Brazzein, A Small, Heat-Stable, Sweet-Tasting Protein, 376 Archives of Biochemistry and Biophysics, 259-265 (2000) there was discussion regarding the N and C termini of Brazzein being important for sweetness (e.g. deletion of one C terminal residue eliminated sweetness).

While these developments are of significant interest, there is still a need for the development of protein sweeteners that provide a highly potent sweetness, particularly when providing a candy-like sweetness.

SUMMARY OF THE INVENTION

The present invention provides a sweet peptide comprising an amino acid sequence selected from the group consisting of SEQ ID NO: 2 (where Xaa is not Tyr) and SEQ ID NO: 3 (wherein at least one Xaa is isoleucine, glycine or proline). Preferred forms of SEQ ID NO: 2 are where the Xaa residue is Phe, Trp or His. Preferred forms of SEQ ID NO: 3 are where residues 1 and 2 are either both isoleucine, or are Gly Pro.

It has been surprisingly learned that the replacement of the tyrosine at position 53 of SEQ ID NO: 1 with another amino acid, or the insertion of two amino acid residues at the N terminus of wild type Brazzein (with at least one isoleucine, glycine or proline), desirably improve sweetness potency and nature. See SEQ ID NOS: 4-8.

Another form of the invention is to provide nucleotide sequences for expressing such peptides. Our most preferred embodiments are SEQ ID NOS: 9-13, when expressing in *E. coli*.

As is well known, a given amino acid can typically be expressed from different codons. Certain hosts (e.g. yeast) can have improved yields when the codons selected are optimized for use in that host. Thus, the nucleotide sequences of the present invention are not to be limited only to the specific examples.

The sweet proteins of the present invention should be useful to sweeten consumable foods and beverages. For example, a small amount of the peptide can be dissolved in iced tea.

Production of genes coding for these peptides (particularly when coding for a desirable fusion protein) and their insertion into production vectors, will allow large quantities of the sweeteners to be created at low cost. Further, it is expected that appropriately configured genes can be inserted directly into a plant genome (and even possibly an animal genome) so that the fruit, vegetables, and/or edible meats, milk or the like may be sweeter.

The advantages of the present invention include providing improved protein sweeteners, which can be detected by humans at concentrations lower than concentrations usually required for Brazzein to be detected, and genes coding for such protein sweeteners. Further, the nature of the sweetness mimics a candy-like sweetness, making the sweeteners particularly desirable.

These and still other advantages of the present invention will be apparent from the description, which follows. The following description is merely of the preferred embodiments. Thus, the claims should be looked to in order to understand the full scope of the invention.

DESCRIPTION OF THE PREFERRED EMBODIMENTS

Figure 1:
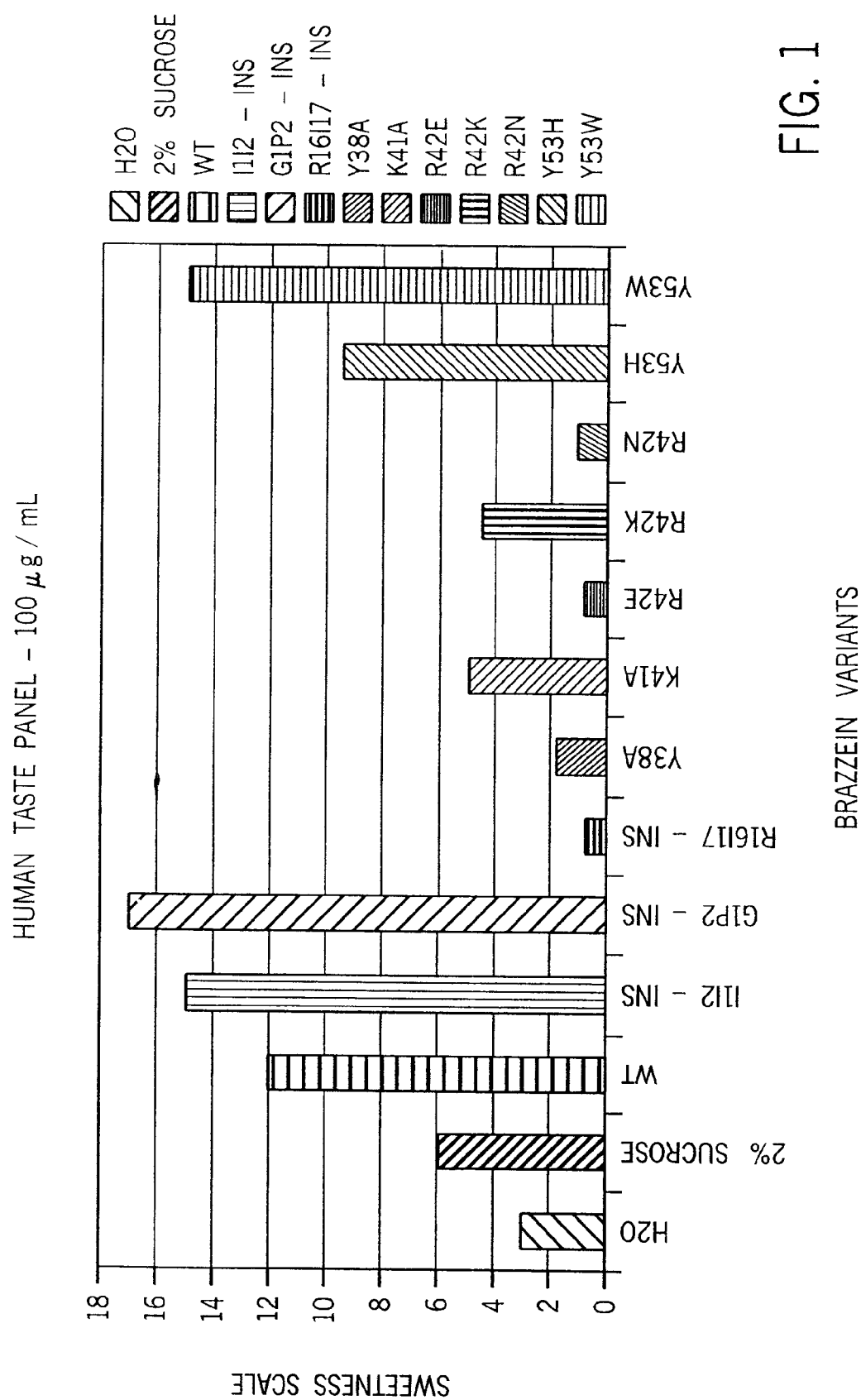
FIG. 1 is a graph depicting the responses of humans regarding the sweetness of various compounds that were tested.

Natural Brazzein can be isolated from *Pentaliplandra brazzeana* as described in WO 94/19467. SEQ ID NO: 1 (natural Brazzein minus the beginning Glu), the Brazzein protein variants described in WO 94/19467, 95/31547 and 00/61759, and DNA coding therefor, can be obtained in accordance with the procedures described in those publications. For example, WO 00/61759 describes one expression vector pET3a/SNase into which DNA coding for mutant Brazzein can be inserted for expression in *E. coli*.

Restriction enzymes and T4 DNA ligase were purchased from Promega (Madison, Wis.). *E. coli* strains, HMS174 (DE3, recA) and BL21(DE3)/pLysS have been purchased from Novagen (Madison, Wis.). Protein expression vector pET-3a was purchased from Novagen (Madison, Wis.). Purchased plasmids were stored in a non-expression host strain HMS174 and expressed in BL21(DE3)/pLysS.

NdeI and Bam HI sites were designed into the 5' and 3' ends, respectively, to permit cloning into the pET system plasmids (characterized by a T7 expression system with an optional fusion to a polyhistidine linker). In addition, a starting codon (Met) was introduced just before the first codon of the synthetic gene, since the amino acid sequence of natural Brazzein lacked an N-terminal methionine.

The DNA for SEQ ID NO. 1 was synthesized by ligating eight oligonucleotides per strand. The Nde I/Bam HI fragment of the resulting DNA, which contained the entire sequence des-Glu-Brazzein, was isolated and cloned into a T7 expression vector. The sequence of the final, ligated expression vector was confirmed by automated DNA sequencing. Mismatches due to errors during synthesis of original oligos were corrected by site-directed mutagenesis using PCR.

The synthetic Brazzein gene was cut with restriction enzymes and cloned into a T7 expression vector of the pET plasmid which contained Nde I and Bam HI sites. The fusion construct was made with a modification of the original nuclease-ovomucoid fusion gene. A. Hinck et al., 6 Prot. Engin. 221-227 (1993).

The four Met codons in the nuclease gene (Snase) were replaced with Ala codons by quick-change site-directed mutagenesis (kit from Stratagene, La Jolla, Calif.). The DNA fragment coding for Brazzein (or the SNase-Brazzein fusion) was excised and cloned between Nde I and Bam HI sites at the C-terminus of the modified Snase gene in the pET-3a expression system. The resulting plasmid, named pET-3a/SNase-SW (see FIG. 1 of WO 00/61759), was transformed into the *E. coli* strain BL21(DE3)/pLysS for protein expression. The use of pLysS in this strain enables expression of the nuclease-Brazzein fusion protein without the deleterious effect of nuclease.

A single colony of *E. coli* strain BL21(DE3)/pLysS, containing the plasmid pET-3a/SNase-SW was selected and grown overnight at 37° C. in 5 mL of Luria Broth medium with 100 µg ampicillin/mL and 34 µg of chloramphenicol/mL. The starting culture was used to inoculate 1 L of LB medium with chloramphenicol (34 µg/mL)/ampicillin (100 µg/mL) at 37° C. until an A600 nm of 0.8-1.0 was attained.

Cells were induced for 3 hours by the addition of isopropyl-β-D-galactopyranoside (IPTG) to a final concentration of 0.2 mM. Cells were harvested and rapidly frozen in liquid nitrogen and stored at −70° C. After freeze/thawing once, 4-5 g of cells were resuspended in 50 mL lysis buffer (50 mM Tris-HCl, pH=8.0, containing 2 mM EDTA and 10 mM PMSF). The lysed cells were treated with 10 mM $CaCl_2$ for a period of 15 minutes and subject to French pressing three times. The fully broken cells were centrifuged for 15 minutes at 12,000 g. The supernatant and the pellet were analyzed on 16% Tricine gels (Novex, San Diego, Calif.). More than 70% of the fusion protein was in insoluble form.

Where protein was present in inclusion bodies, the cell pellet after the French press steps was washed three times with lysis buffer. An extra wash step was carried out to ensure further purity of the inclusion body by adding nine volumes of lysis buffer containing 0.5% (v/v) Triton X-100 and 10 mM EDTA, waiting 5 minutes, and then centrifuging at 5,000×g for 10 minutes at 4° C.

The pellet was resuspended in 50 mL 8 M guanidinium chloride containing 10 mM EDTA and 100 mM DTT and stirred for 2-3 hours at room temperature. The clear resuspension was dialyzed overnight at 4° C. against 4 L deionizer water ($dH_2O$) containing 3.5 mL acetic acid (pH −3.8-4.0) to ensure full protonation of the cysteine side chains. The precipitate was removed by centrifuging at 12,000×g.

The clear supernatant was dialyzed two more times against $dH_2O$ and acetic acid for a total period of 24 hours to completely remove the reducing agent. At this stage, more than 60-70% of the fusion protein was refolded, and the purity, as judged by gel electrophoresis, was greater than 80%. The typical yield of the fusion protein was 130-150 mg/L culture. The reduced sulfhydryl groups in the Brazzein domain were oxidized by rapidly diluting the dialysate with 4-5 volumes of 200 mM Tris-acetic acid, pH 8.0, to a final concentration of 0.5-0.7 mg/mL (based on the SNase extinction coefficient, ε280, 1%=1.0), and this solution was stirred at room temperature for 24 hours. Following the oxidization step, the solution was concentrated with an Amicon ultrafiltration apparatus to a final volume of 20-50 mL. When successfully folded and oxidized, the product was a clear solution. The concentrated fusion protein was dialyzed three times against 10 L of $dH_2O$ to remove residual salt and lyophilized as white powder.

Lyophilized fusion protein (130-150 mg) was dissolved in 65-75 mL water to a final concentration of 2 mg/mL. The pH of the sample was adjusted to 1.5 by adding 1 M HCl. Approximately 70-100 mg of CNBr was added to this solution, which was then stirred in the dark at room temperature for 12 hours. The cleaved product was lyophilized 4 times out of $dH_2O$ to ensure the complete removal of CNBr.

The white powder was dissolved in double distilled water to concentration of 3 mg/ml and was applied to a reverse phase HPLC C18 column (15 cm×1 cm). By raising the percentage of the buffer (70% $CH_3CN$, 0.1% TFA) from 10 to 55, correctly folded and desalted Brazzein proteins were eluted and separated from the nuclease and uncleaved fusion protein. Brazzein-containing fractions were combined and lyophilized.

An alternative approach is to insert six histidine amino acids at the C-terminus of Snase before linking to Brazzein. This fusion construct would then allow use of a nickel-NTA column chromatography to purify Brazzein from uncut Snase-Brazzein fusion material, and Snase proteins, prior to the final HPLC purification. To achieve this we used an elution buffer which was 20 mM $Na_2HPO_4$, 0.3 M NaCl pH 8.0 to elute Brazzein.

Yet another approach would be to use an expression system referred to as the "SUMO" expression system, offered by Life Sensors. See generally R. Butt, SUMO Fusion Technology For Difficult-To-Express Protein, 43 Protein Expr. Purif. 1-9 (2005). We have successfully linked the Brazzein gene to the 3' end of the SUMO gene and then used 0.5 mM IPTG to induce cells for 24 hours at 25° C. Cells were lysed by sonication. The soluble fraction was applied to nickel-NTA column chromatography and fusion protein was eluted at greater than 90% purity. The fusion protein was then cleaved by SUMO protease at high efficiency and purified using reverse phase HPLC. This SUMO alternative is expected to enhance expression of constructs, as well as facilitate production through improved solubility and folding. The SUMO-Brazzein system can then be expressed in either bacteria or yeast.

In any event, DNA sequences coding for the SEQ ID NOS. 4-8 Brazzein variants were prepared by site directed mutagenesis using the parental vector containing the DNA for SEQ ID NO. 1. Basically, we followed the Quick Change™ PCR kit protocol from Stratagene, with the following variations:

To create SEQ ID NO. 4 we used an oligo having the SEQ ID NO. 14 sequence.

To create SEQ ID NO. 5 we used an oligo having the SEQ ID NO. 15 sequence.

To create SEQ ID NO. 6 we used an oligo having the SEQ ID NO. 16 sequence.

These sequences were used to make mutations in the parental wild-type Brazzein using pET3a vector which contains the modified Snase fusion. Basically, 20 ng of template wild type Brazzein DNA was mixed with 125 ng of each of the complementary primers applicable to each PCR reaction. After 16-18 PCR cycles the reaction was treated with 10 units of DpnI at 37° C. for one hour to remove the original template DNA.

A somewhat similar approach was used for two amino acid insertions (after a Met at the junction between Snase and the Brazzein fusion protein). However, we prefer making one insertion at a time. Hence, to create the Ile Ile insertion we first inserted one amino acid residue using the SEQ ID NO. 17 oligo. After obtaining a sequence with one Ile insertion, we then used the SEQ ID NO. 18 sequence to insert the second Ile.

In an analogous fashion, the Gly/Pro insertion was inserted by first inserting only Gly using SEQ ID NO. 19, and then using SEQ ID NO. 20 to insert Pro.

To test the sweetness potency of our peptides we tested human perception of sweetness against known controls using varied concentrations of the protein (or other substance) being diluted in water. In the taste panel, humans were requested to score the sweetness sensations of the stimuli with a magnitude labeled scale in accordance with the techniques of B. Green et al., 21 Chemical Senses 323 (1996) (e.g. barely detectable; weak; moderate; strong; very strong; strongest imaginable).

We first gave those testers a sample of pure water with 2-10% sucrose as a calibration exercise two hours before protein testing. After the sucrose testing, they rinsed their mouth out thoroughly. The normal protocol included applying about 125 μl of the substance being tasted to the tongue, with the tested material kept in the mouth for about a minute.

As can be seen from FIG. 1, the proteins of SEQ ID NOS. 5, 7 and 8 (Y53W, I1I2-ins and G1P2-ins) had significantly higher sweetness potency than either sucrose or wild type Brazzein, for the weight being tested. The protein of SEQ ID NO. 6 (Y53H) had significantly higher sweetness potency than sucrose for the weight being tested (while also having a desirable taste profile relative to wild type Brazzein).

AS yet, we have not had a complete panel test SEQ ID NO. 4. However, it was tested by an individual observer who reported results similar to those for SEQ ID NO. 5.

Moreover, the reported nature of the taste for SEQ ID NOS. 4-8 was for each peptide purely sweet without detectable sourness, saltiness or bitterness, and was particularly thought to resemble candy sweetness of a pleasant nature (like sugar cane). These SEQ ID NOS. 4-8 variants therefore are excellent candidates for use alone, and/or in combination with other sweeteners, and/or in combination with each other. When used as the peptide (instead of as a DNA sequence expressing the peptide), e.g. as a food or beverage sweetener, a blend of a mutant with other known sweeteners may be desirable to most closely mimic sugar or some other desired taste. These sweetness results are unexpected. In this regard, deletion of Tyr 53 (without replacement) greatly reduces sweetness to only slightly sweet in the powder form. Further, a variety of other substitutions of a single amino acid for another single amino acid decrease sweetness potency, or have less desirable sweetness properties. In this regard, we include in FIG. 1 examples of five substitutions which reduced sweetness potency relative to the wild type, and an example of an insertion that had a similar result.

As another example of the surprising nature of these results, we note that a variety of other changes at the N terminal adversely affect sweetness. For example, adding a Glu at the beginning of wild type Brazzein (to convert to its other natural alternative form) reduces the sweetness potency substantially. Nevertheless, adding two amino acids, where at least one is isoleucine, glycine or proline, increases potency.

Another benefit is that nearly one seventh of the amino acid composition of these peptides is lysine, an essential amino acid. Moreover, other Brazzein variants have shown desirable heat stability. Thus, these proteins may also be suitable for use in baking applications.

Given that these peptides are so sweet, only a very small amount of them should be needed to sweeten coffee, tea, or the like to the desired level of sweetness. For such uses, it is expected that they will be blended with a bulky filler (e.g. lactose) to give the user a feeling of perceived value and to ease consumer handling.

If one desires to produce these proteins in large quantity, one could synthesize the desired one of SEQ ID NOS: 9-13 using techniques analogous to those noted above, or by combining standard cloning and automated synthesizer techniques (e.g. 380 B ABI DNA synthesizer). Each gene could then be cloned into an expression vector such as those described above. Such vectors could then be inserted into suitable hosts such as BL21 (DE3/pLysS or BL21-CodonPlus (DE3) RIPL (Strategene), with expression in the usual manner.

The protein can then be harvested in the usual way (e.g. as part of a fusion protein). If desired, modifications can be made in conventional ways to reduce or eliminate undesired portions of the fusion proteins.

While production in bacteria, yeast or another cellular host is one technique, other means of producing the protein are also intended to be within the scope of the invention, such as direct synthesis using a peptide synthesizer, or synthesis in transgenic plants bearing the recombinant sequence. In this regard, as noted above, it should also be possible to insert the cDNA into plant or animal genomes using known means to cause the gene to be expressed (thereby creating sweeter fruit, vegetables or meats). Thus, when we use the term "synthetically produced peptide" we mean all of these techniques (even though a living host such as a plant, as distinguished from a laboratory vessel, might be involved).

INDUSTRIAL APPLICABILITY

The invention provides sweet proteins that can, among other things, be added to or expressed in consumable items to impart a sweet flavor, and nucleotides useful to produce them.

I claim:

1. A peptide consisting of:
    SEQ ID NO: 2 wherein the Xaa at position 53 is selected from the group consisting of Phe, Trp or His;
    SEQ ID NO: 3 wherein the Xaa-Xaa at positions 1 and 2 is selected from Ile-Ile or Gly-Pro;
    wherein the peptide has a different sweetness potency from naturally occurring Brazzein.

2. The peptide of claim 1 consisting of SEQ ID NO: 2 wherein the Xaa at position 53 is selected from the group consisting of Phe, Trp or His.

3. The peptide of claim 2 wherein the Xaa at position 53 is Phe.

4. The peptide of claim 2 wherein the Xaa at position 53 is Trp.

5. The peptide of claim 2 wherein the Xaa at position 53 is His.

6. The peptide of claim 1 consisting of SEQ ID NO: 3 wherein the Xaa-Xaa at positions 1 and 2 is selected from Ile-Ile and Gly-Pro.

7. The peptide of claim 6 wherein the Xaa-Xaa at positions 1 and 2 is Ile-Ile.

8. The peptide of claim 6, wherein the Xaa-Xaa at positions 1 and 2 is Gly- Pro.

* * * * *